(12) United States Patent
Ootsubo

(10) Patent No.: US 8,394,090 B2
(45) Date of Patent: *Mar. 12, 2013

(54) MEDICAL DEVICE

(75) Inventor: Seiichi Ootsubo, Tokyo (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1258 days.

This patent is subject to a terminal disclaimer.

(21) Appl. No.: 12/145,208

(22) Filed: Jun. 24, 2008

(65) Prior Publication Data

US 2008/0319439 A1 Dec. 25, 2008

(30) Foreign Application Priority Data

Jun. 25, 2007 (JP) ................... 2007-166786

(51) Int. Cl.
*A61B 18/18* (2006.01)

(52) U.S. Cl. ........................................... 606/41

(58) Field of Classification Search ..................... 606/41
See application file for complete search history.

(56) References Cited

U.S. PATENT DOCUMENTS

| | | | |
|---|---|---|---|
| 5,827,268 A | 10/1998 | Laufer | |
| 5,919,200 A | 7/1999 | Stambaugh et al. | |
| 6,004,316 A | 12/1999 | Laufer | |
| 6,939,348 B2 | 9/2005 | Malecki et al. | |
| 7,165,552 B2 | 1/2007 | Deem et al. | |
| 7,186,251 B2 | 3/2007 | Malecki et al. | |
| 7,257,450 B2 | 8/2007 | Auth et al. | |
| 7,293,562 B2 | 11/2007 | Malecki et al. | |
| 7,311,701 B2 | 12/2007 | Gifford et al. | |
| 2004/0193147 A1 | 9/2004 | Malecki et al. | |
| 2004/0230185 A1* | 11/2004 | Malecki et al. | 606/2 |
| 2004/0243122 A1 | 12/2004 | Auth et al. | |
| 2004/0267191 A1 | 12/2004 | Gifford, III et al. | |
| 2005/0033288 A1 | 2/2005 | Auth et al. | |
| 2005/0080406 A1 | 4/2005 | Malecki et al. | |
| 2005/0131401 A1 | 6/2005 | Malecki et al. | |
| 2005/0131460 A1 | 6/2005 | Gifford, III et al. | |
| 2005/0192626 A1 | 9/2005 | Widomski et al. | |
| 2005/0192654 A1 | 9/2005 | Chanduszko et al. | |
| 2005/0209636 A1 | 9/2005 | Widomski et al. | |
| 2005/0216054 A1 | 9/2005 | Widomski et al. | |
| 2006/0027241 A1 | 2/2006 | Malecki et al. | |
| 2006/0074410 A1 | 4/2006 | Malecki et al. | |

(Continued)

FOREIGN PATENT DOCUMENTS

| | | |
|---|---|---|
| JP | 11-19091 A | 1/1999 |
| JP | 2002-503969 A | 2/2002 |

(Continued)

OTHER PUBLICATIONS

Extended European Search Report issued in EP 08 15 9038, Dec. 17, 2008, EPO, Munich, DE.

*Primary Examiner* — Nicholas Lucchesi
*Assistant Examiner* — Jenna Zhang
(74) *Attorney, Agent, or Firm* — Buchanan Ingersoll & Rooney PC

(57) ABSTRACT

A medical device for fusing or necrosing biological tissue includes a pair of electrode members configured to sandwich the biological tissue, and an energy supply unit configured to supply electric energy to between the pair of electrode members, wherein the surface area of each of the pair of electrode members is mutually different.

18 Claims, 9 Drawing Sheets

U.S. PATENT DOCUMENTS

| | | |
|---|---|---|
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 * | 11/2006 | Francis et al. .................. 606/27 |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |
| 2007/0027445 A1 | 2/2007 | Gifford et al. |
| 2007/0044811 A1 | 3/2007 | Deem et al. |
| 2007/0078485 A1 | 4/2007 | Deem et al. |
| 2007/0088355 A9 | 4/2007 | Auth et al. |
| 2007/0093804 A1 | 4/2007 | Kaveckis et al. |
| 2007/0093805 A1 | 4/2007 | Auth et al. |
| 2007/0100324 A1 | 5/2007 | Tempel et al. |
| 2007/0106214 A1 | 5/2007 | Gray et al. |
| 2007/0112347 A1 | 5/2007 | Malecki et al. |
| 2007/0123824 A1 | 5/2007 | Kaveckis |
| 2007/0123851 A1 | 5/2007 | Alejandro et al. |
| 2007/0123852 A1 | 5/2007 | Deem et al. |
| 2007/0203479 A1 | 8/2007 | Auth et al. |
| 2007/0287999 A1 | 12/2007 | Malecki et al. |
| 2007/0299434 A1 | 12/2007 | Malecki et al. |
| 2008/0004658 A1 | 1/2008 | Malecki et al. |
| 2008/0009859 A1 | 1/2008 | Auth et al. |
| 2008/0058683 A1 | 3/2008 | Gifford et al. |
| 2008/0140064 A1 | 6/2008 | Vegesna |
| 2008/0140068 A1 | 6/2008 | Taimisto |
| 2008/0140069 A1 | 6/2008 | Filloux et al. |
| 2008/0140070 A1 | 6/2008 | Filloux et al. |
| 2008/0140071 A1 | 6/2008 | Vegesna |
| 2008/0140074 A1 | 6/2008 | Horne et al. |
| 2008/0140112 A1 | 6/2008 | Horne |
| 2008/0140113 A1 | 6/2008 | Taimisto et al. |
| 2008/0140170 A1 | 6/2008 | Filloux et al. |

FOREIGN PATENT DOCUMENTS

| | | |
|---|---|---|
| JP | 2006-047636 | 2/2006 |
| JP | 2006-521181 A | 9/2006 |
| WO | 96/23449 A1 | 8/1996 |
| WO | WO 99/18871 A1 | 4/1999 |
| WO | WO 2004/086944 A2 | 10/2004 |
| WO | WO 2006/127970 A2 | 11/2006 |
| WO | WO 2006127970 A2 * | 11/2006 |
| WO | WO 2007/030433 A2 | 3/2007 |
| WO | WO 2007/038609 A2 | 4/2007 |
| WO | WO 2007/100067 A1 | 9/2007 |
| WO | WO 2007/140419 A2 | 12/2007 |

* cited by examiner

MEDICAL DEVICE

This application is based on, and claims priority under 35 U.S.C. §119(a) with respect to, Japanese Patent Application No. 2007-166786 filed Jun. 25, 2007, the entire content of which is hereby incorporated by reference.

TECHNOLOGICAL FIELD

The present invention generally relates to a medical device which closes a defect occurring in a living body and more specifically pertains to such a medical device with electrode members sandwiching a biological tissue.

BACKGROUND DISCUSSION

Recently, patent foramen ovale (hereinafter referred to as PFO) has been cited as a cardiogenic factor in a stroke and a hemi headache. PFO is a defect in the septum between the two upper (atrial) chambers of the heart. More specifically, PFO is an incomplete closure of the atrial septum so that a flap or valve-like opening exists in the atrial septal wall. It is said that PFO exists in 20 to 30% of adults.

The foramen ovale occurs at a septum secundum (Septum Secundum, hereinafter, referred to as atrial septum) of the heart and the pressure on the left atrium side exceeds the pressure on the right atrium side in the heart on a normal occasion, so that it is occluded by a septum primum (Septum Primum, hereinafter, referred to as foramen ovale valve). But when the pressure on the right atrium side exceeds the pressure on the left atrium side on the occurrence of a strain (for example, when coughing, when holding on) or the like, the foramen ovale valve opens to the left atrium side and blood flows from the right atrium side (venous side) into the left atrium side (arterial side). When a thrombus is included in this blood, the thrombus is shifted from the venous side to the arterial side, flows along a route involving left atrium→left ventricle→aorta→brain, and can become a factor in a stroke, hemi headache or the like.

To treat PFO, the use of a percutaneous catheter procedure is considered desirable if the same effect as open heart surgery can be obtained.

A closing technique device using the percutaneous catheter can be used also in case of closing defects such as a congenital atrial septum defect (ASD), a PFO, a ventricular septal defect (VSD) and a patent ductus arteriosus (PDA). A device in the past is a device sandwiching the foramen ovale valve and the atrial septum by using disk-shaped membranes or anchor members for closing the defect and which are indwelled in the body.

A PFO closing device described in WO2004/086944 A2 (Patent Document 1) is a device in which an apparatus is inserted into the foramen ovale from the right atrium toward the left atrium, a foramen ovale valve is pulled to the foramen ovale so as to close it, and the tissue is to be sutured by applying electric energy. The PFO closing device should preferably be able to address a foramen ovale, foramen ovale valve and atrial septum which differ in terms of size (smaller versus larger), thicknesses, shape and the like depending on the individual and according to circumstances.

Japanese Patent Application No. 2006-47636 (Patent Document 2) discloses a PFO closing device in which the foramen ovale valve and the atrial septum are sandwiched by a pair of electrodes, and the tissue is sutured by applying electric energy from both electrodes.

SUMMARY

According to one aspect, a method for fusing or necrosing a biological tissue involves positioning a first electrode member on one side of biological tissue, the first electrode member comprising a first electrode surface possessing an electrode surface area, positioning a second electrode member on an opposite side of the biological tissue, the second electrode member comprising a second electrode surface possessing an electrode surface area that is different from the electrode surface area of the first electrode surface, and supplying electric energy between the first electrode surface and the second electrode surface while the biological tissue is sandwiched between the first electrode surface and the second electrode surface to fuse or necrose the biological tissue.

According to another aspect, a medical device for fusing or necrosing a biological tissue comprises a first electrode member possessing a size positionable in a living body on one side of biological tissue, a second electrode member possessing a size positionable in the living body on an opposite side of the biological tissue, and an energy supply unit configured to supply electric energy to between the first and second electrode members. The first electrode member possesses an electrode surface, and the first electrode member is positionable in the living body so that the electrode surface of the first electrode member is positioned on a front side of the biological tissue. The second electrode member comprises a needle-shaped electrode member configured to stick the biological tissue so that the needle-shaped electrode member extends from the front side of the biological tissue through the biological tissue to a side of the biological tissue opposite the front side of the biological tissue. The needle-shaped electrode member possesses an electrode surface, and is positionable in the living body so that the electrode surface of the needle-shaped electrode member is positioned beyond the biological tissue by the sticking of the biological tissue. The electrode surface of the first electrode member possesses an electrode surface area, and the electrode surface of the needle-shaped electrode member possesses an electrode surface area. The electrode surface area of the electrode surface of the needle-shaped electrode member is larger than the electrode surface area of the electrode surface of the first electrode member.

In accordance with a further aspect, a medical device for fusing or necrosing a biological tissue includes two electrode members configured to sandwich the biological tissue between the pair of electrode members, and an energy supply unit to supply electric energy between the two electrode members to effect the fusing or necrosing of the biological tissue while the biological tissue is sandwiched between the two electrode members. Each of the two electrode members comprises an electrode surface which possesses a surface area, with the surface area of the electrode surface of one of the two electrode members being different from the surface area of the electrode surface of the other electrode member.

The medical device and method at issue here are able to avoid attachment of a thrombus to be the electrode(s), even when electric energy is applied in the blood, and it is possible to perform a relatively safe and reliable procedure for fusing or necrosing the tissue.

By supplying electric energy to biological tissue using electrode members in which the electrode surface area of each of the electrode members for fusing or necrosing this tissue is mutually different, it is possible to restrict the region which can supply electric energy with respect to the biological tissue. It is thus possible to avoid situations in which the temperature of the electrode members is increased unnecessarily, and the possibility of a thrombus attaching by coagulating blood flowing at the periphery of the electrode members is lessened.

Coating at least one of the two electrode members with an electrical insulation body (electrical insulator) helps permit control of the electric energy concentration transmitted from the respective electrode members to the biological tissue. Thus, for example, even if an extremely thin member such as a needle is used for the electrode members (one of the electrode members), it is possible for the temperature increase and the resultant attachment of a thrombus caused by the electric energy concentration to be inhibited or prevented from occurring.

Using a needle-shaped electrode member as at least one of the electrode members so that the needle-shaped electrode member is able to stick the biological tissue, it is possible to generally stabilize the installation condition of the electrode members by the sticking, whatever the nature of the biological tissue, and the sandwiching of the tissue by the two electrode members is easier.

If the other of the two electrode members is a flat plate-shaped electrode member, the contact area with the biological tissue can be secured and also, even in a case in which the biological tissue is sandwiched with respect to the needle-shaped electrode member, the sandwiching becomes easier and also the procedure becomes safer and easier.

In particular, in case of treatment using a membrane-like member positioned between the left atrium and the right atrium of the heart, if a coating of an electrical insulation body (electrical insulator) is applied such that the area (S1) of the electrode surface of the right atrium side electrode member is smaller than the area (S2) of the electrode surface of the left atrium side electrode member, and in the case of supplying electric energy by energizing between the two electrode members, electric energy concentration will relatively easily occur at the right atrium side electrode member and it is possible to inhibit or prevent the temperature increase. Also, the resultant attachment of a thrombus, caused by the electric energy concentration at the left atrium side electrode member, is less likely to occur.

If the aforementioned needle-shaped electrode member is configured so that it expands and widens toward the distal side from the attachment portion, it is possible to hold the biological tissue in a wider region, the grip becomes more certain, the fusion becomes easier, the fusion force is improved and the thrombus attachment is reduced.

If the proximal side of the two electrode members is held at the attachment portion composed of an electrical insulation member, it is possible, based on a relatively simple construction, to make a construction in which electric power supplied to the electrode members will not flow on the hand side of the surgery operator.

By making the electrode area adjustable, for example by adjusting a protruding length of at least one electrode member from the attachment portion, adjustment of electric energy supply can be executed by putting the electrode member into or out of the attachment portion. Even in the case of different types of biological tissues or biological tissues different in nature, it is possible to deal with these and it is possible to attempt simplification of the procedure, readiness, assurance and speeding-up.

If the surface of the electrode member is coated with an electrically-conductive material to which biological tissue cannot easily attach, a thrombus or blood, attachment of a thrombus can be inhibited or prevented much more reliably.

If the area ratio (S1/S2) between the surface area (S2) of the electrode surface at the left atrium side electrode member and the surface area (S1) of the electrode surface of the right atrium side electrode member is more than 0.6 to less than 1.0, it becomes difficult for a thrombus to attach to either one of the electrode members, and the procedure becomes easier.

Using an attachment portion constituted by a catheter provided in a guiding catheter, the device and method become relatively simple and it is possible to simplify the procedure.

When a positioning mechanism for positioning one electrode member at a predetermined position with respect to the foramen ovale is provided in this medical device, the sticking becomes accurate and certain when sticking to a tissue such as a foramen ovale valve or an atrial septum and the like is executed, and it is possible to make also the procedure of the suturing operation more accurate, more speedy and also easier.

Providing the medical device with a positioning hold mechanism composed of a positioning portion for positioning one electrode member with respect to the foramen ovale and a holding portion for holding the foramen ovale valve with respect to the other electrode member so as not to allow the backward movement thereof, such operations referred to as positioning and holding the foramen ovale valve can be carried out together. Also, even in the case of a thin-walled foramen ovale valve, the sticking can be executed for a predetermined position without breaking or hurting that valve. Thus safety and simplification of the procedure are improved and it is possible to perform the procedure relatively accurately and also more speedily.

By providing the energy supply unit as a high frequency bipolar system for controlling the electric current by the impedance of the biological tissue between both aforesaid electrode members, it can have correspondence easily in response to the state of the tissues of the foramen ovale valve and the atrial septum which differ depending on a person, and the safety and the convenience of the procedure are obtained.

If one electrode member is a needle-shaped electrode member for sticking the biological tissue, the needle-shaped electrode member is arranged for the electrode surface thereof at a position extending beyond the biological tissue by the sticking, and the electrode surface of the other electrode member is arranged on the front side of said biological tissue. Here, the area (S3) of the electrode surface of the needle-shaped electrode member is made larger than the area (S4) of the electrode surface of the other electrode member. Even in a case in which it is hard to sandwich a biological tissue at a periphery of a defect such as, for example, in a case of an atrial septum defect or the like, it becomes sandwichable by both the electrode members comparatively easily when displacing the biological tissue directed to the other electrode member after executing the sticking by the needle-shaped electrode member.

Also, by doing like this, in such a case in which the blood flow is directed from the other electrode member side on the front side to aforesaid needle-shaped electrode member, it happens that also such an effect that it becomes difficult for the thrombus to be attached to the downstream side of the flow will be presented.

If the other aforesaid electrode member is constituted by a flat plate-shaped electrode member, the sandwich between the electrode members becomes relatively easy and also the procedure becomes more safe and easy.

If the area ratio (S4/S3) between the surface area (S3) of the electrode surface of the aforesaid needle-shaped electrode member and the surface area (S4) of the electrode surface of aforesaid other electrode member is made to be more than 0.6 to less than 1.0, it is more difficult for both the electrode members to be attached with a thrombus and the procedure becomes easier.

BRIEF DESCRIPTION OF THE DRAWING FIGURES

DETAILED DESCRIPTION

Figure 1:
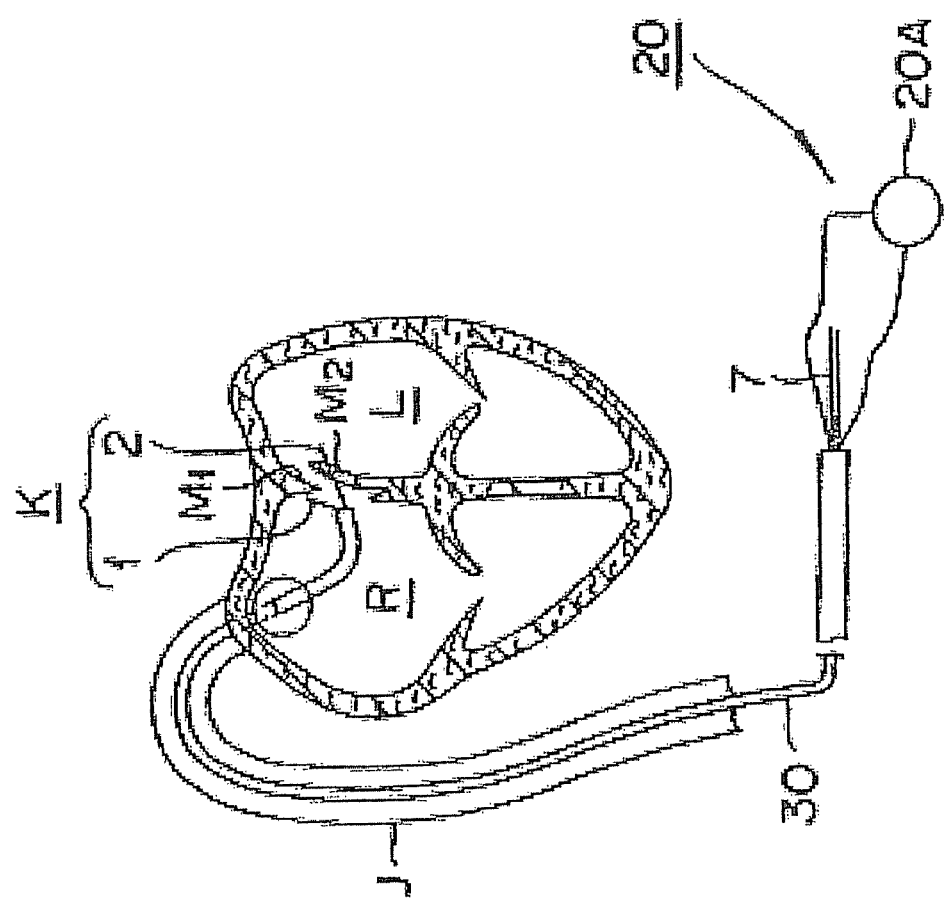
FIG. 1 is a schematic cross-sectional view of a medical device for PFO closing as disclosed herein.

Referring initially to FIG. 1, a medical device for PFO includes a damper K, comprised of a first electrode member 1 and second electrode member 2, which is installed or positioned in a percutaneous catheter 30. In the illustrated position, the medical device is illustrated sandwiching biological tissues M. More specifically, the medical device is illustrated sandwiching a foramen ovale valve M2 (membrane-like member) and an atrial septum M1 (membrane-like member) by way of the damper K. Electric energy from an energy supply unit 20 is supplied to the sandwiched foramen ovale valve M2 and atrial septum M1 to fuse (suture) them.

In the drawing, J denotes the inferior vena cava, L denotes the left atrium and R denotes the right atrium.

Figure 2:
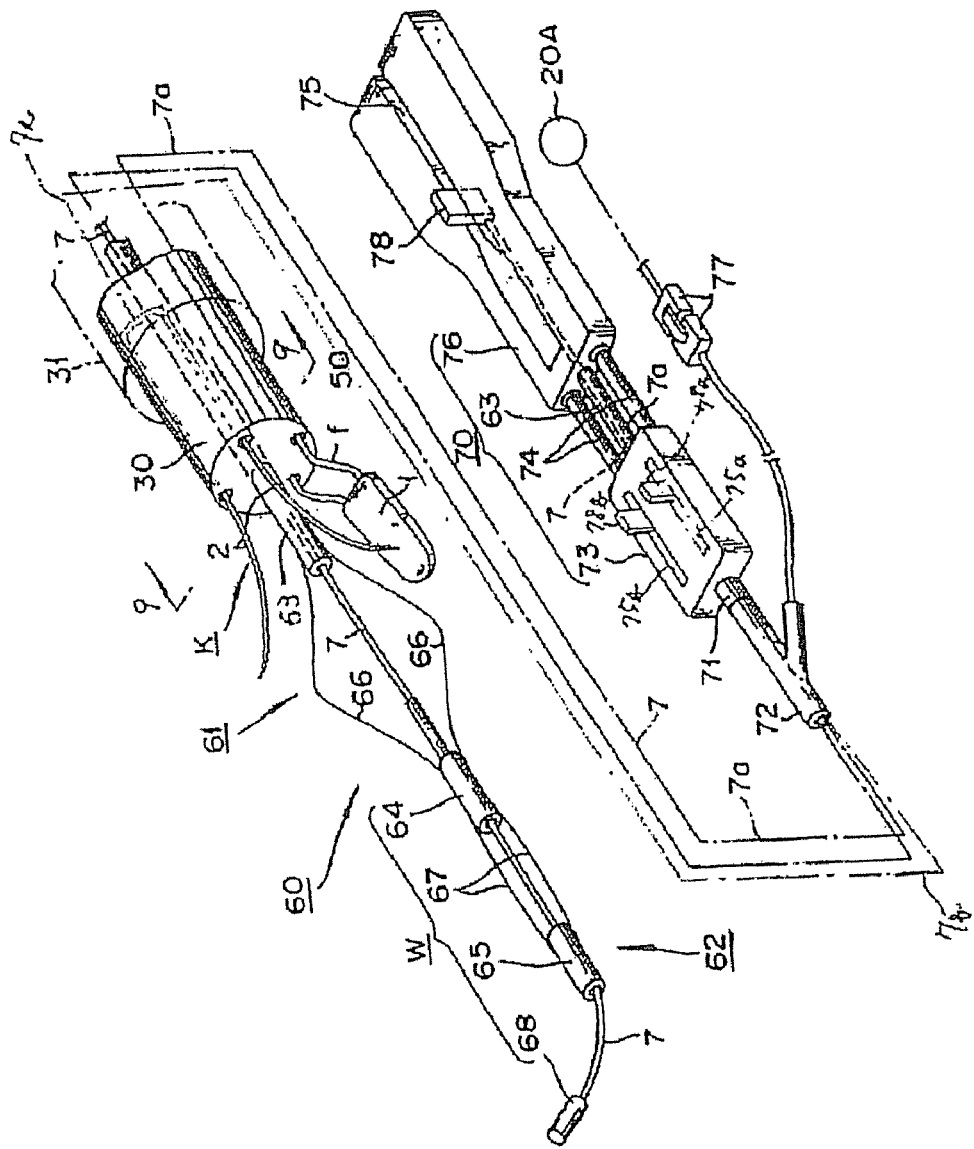
FIG. 2 is a perspective view of the medical device shown in FIG. 1.

Referring to FIG. 2, the medical device includes a hand-operated operation unit 70 provided on the proximal side, a guiding catheter 31 mounted on the operation unit 70 for the proximal tip thereof; a catheter 30 provided in the guiding catheter 31, a positioning hold mechanism 60 provided at a distal portion of the catheter 30, a support body 50 position-fixed at the distal portion in the inside of the catheter 30; and a damper K provided in the support body 50. In the following explanation, the operation unit side of the medical device is referred to as the proximal side and the damper K side or the foramen ovale valve M2 side is referred to as the distal side.

Figure 3:
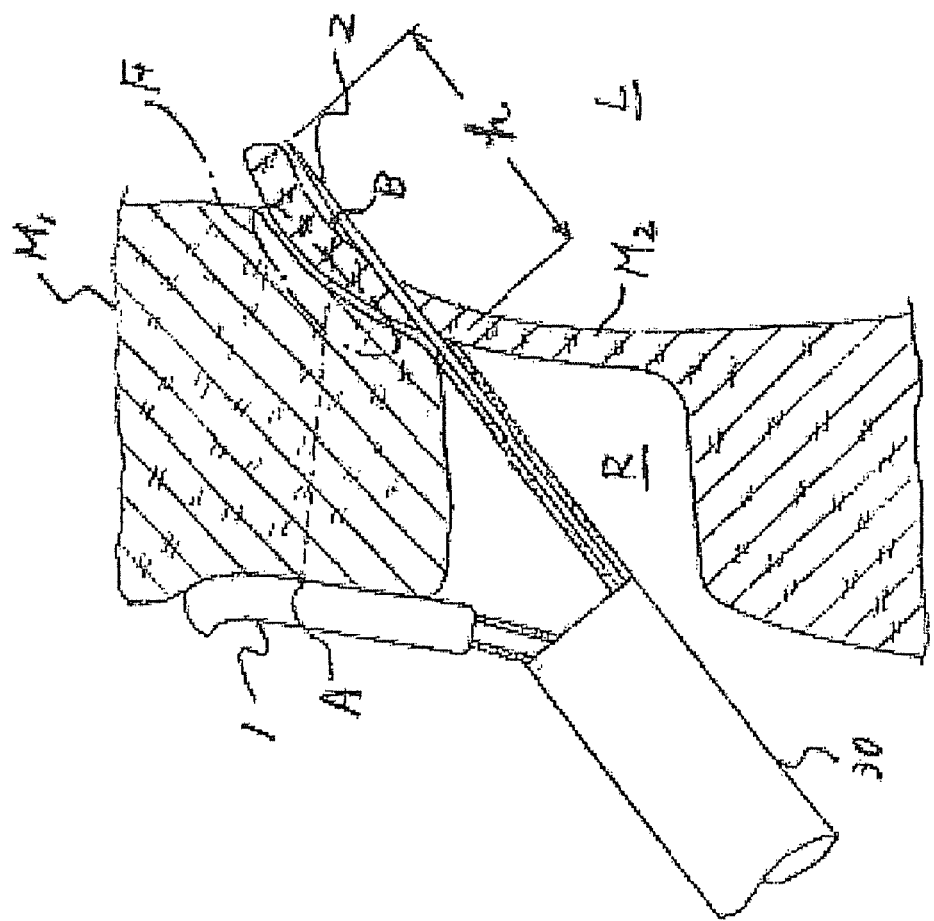
FIG. 3 is a schematic cross-sectional view showing a state in which a foramen ovale valve and an atrial septum are sandwiched by a pair of electrode members.
Figure 4:
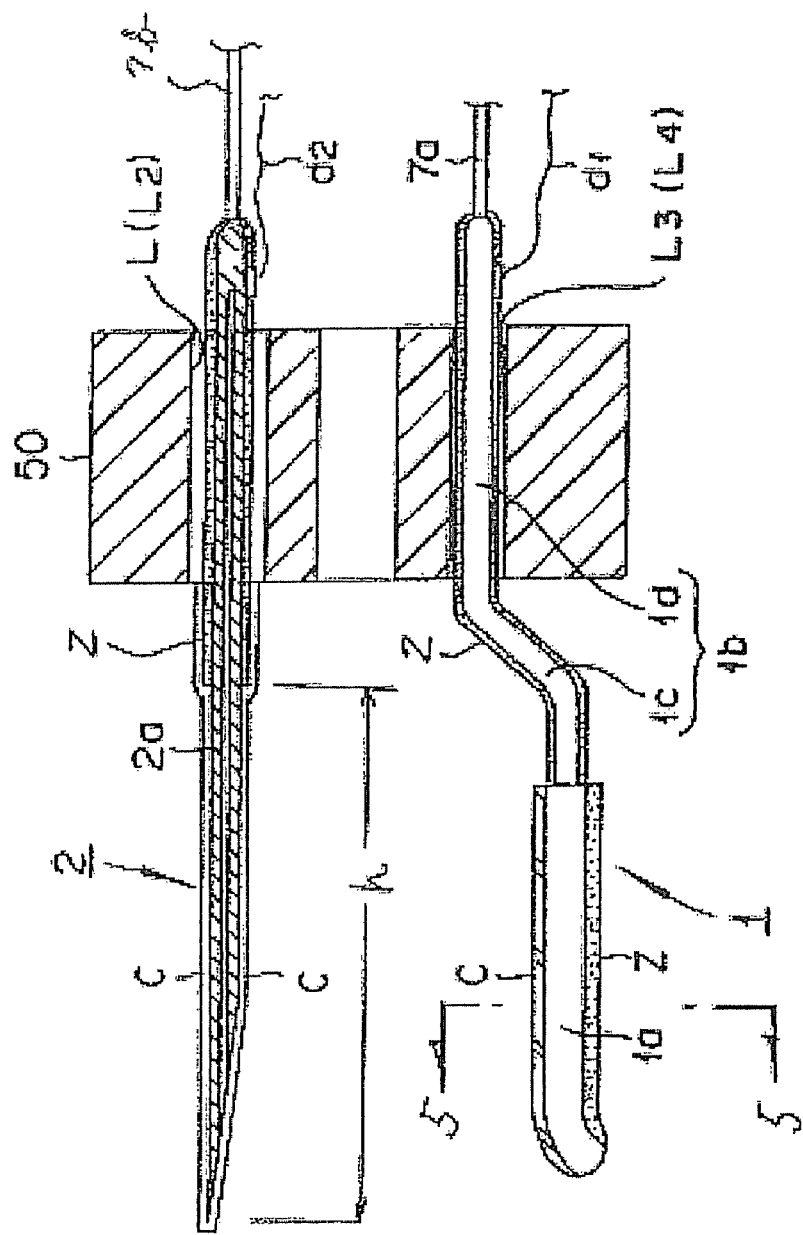
FIG. 4 is a cross-sectional view of a clamper.

The damper K comprises, as shown in FIG. 3, the first electrode member 1 adapted to directly contact one side surface of the atrial septum M1 and the second electrode member 2 which is adapted to be stuck into the foramen ovale valve M2. As shown in FIG. 4, the proximal portion of both the electrode members 1, 2 are held at the support body 50 and protrude from the support body 50 in a manner generally facing each other.

The first electrode member 1 comprises a main body portion 1a formed in an electrically-conductive flat plate shape and a pair of wire portions 1b connected to the proximal portion of the main body portion. Each wire portion 1b includes a bend portion 1c and a straight-shaped portion 1d. The straight-shaped portions 1d are positioned in respective lumens L3, L4 of the support body 50, and a one piece operation member 7a and a conductive wire d1 are provided (connected) on the proximal side of the wire portions 1b. Therefore, if the operation member 7a coupled to the first electrode member 1 is moved or pulled, the bend portion 1c moves into the entrance portion of the lumens L3, L4 of the support body 50, and so the first electrode member 1 approaches towards and moves away (separate) from the second electrode member 2. It is thus possible to carry out the sandwiching of the biological tissue by both the electrode members relatively easily and smoothly, even when using a catheter 31 having a relatively thin distal portion.

A SUS material can be used for the material of the main body portion 1a, though it is preferable to use a material which does not exert a bad influence on a living body such as, for example, gold, silver, platinum, tungsten, palladium or alloys of these, Ni—Ti alloy, titanium alloy or the like.

The first electrode member 1 is constituted by a flat plate-shaped electrode member, so that the contact area with the biological tissue can be secured. Also, even if the second electrode member 2 is a needle-shaped electrode member, which will be described later, the sandwiching becomes relatively easy and also the procedure becomes comparatively safe and easy when the biological tissue M is sandwiched with respect to the second electrode member 2.

With respect to the second electrode member 2, a portion of the second electrode 2 protrudes from the support body 50, the latter of which serves as an attachment portion. The second electrode member 2 is comprised of a pair of elongated needle-shaped (electrode) members 2a having circular or ring-shaped cross-sections perpendicular to the axis of the respective elongated members. With needle-shaped electrode members, it is possible to better stabilize the installation condition of the electrode members by sticking whichever mode of biological tissue it is, and the sandwiching by both the electrode members becomes relatively easy. The proximal sides or ends of the needle-shaped members 2a are positioned in the lumens L1, L2 respectively.

It should be noted that the first electrode member 1 is described as a plate-shaped electrode member, but it is not limited only to this configuration. It is also possible to construct it as, for example, a needle-shaped electrode member similar to the second electrode member 2.

Figure 6:
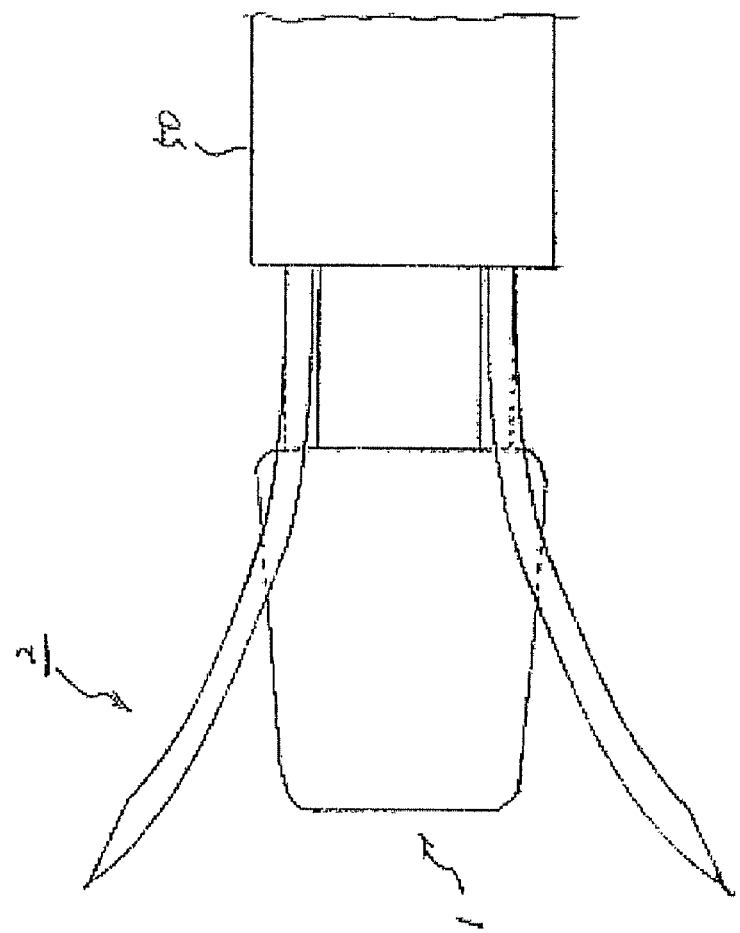
FIG. 6 is a plan view of the damper shown in FIG. 4.

The second electrode member 2 may be a member which protrudes linearly in parallel (e.g., with parallel members) or expands a little bit toward the distal side (e.g., slightly diverging members). However, as shown in FIG. 6, it is preferable that the second electrode member 2 be constructed to expand or diverge in a manner widening toward the distal side from the support body 50. With this construction, it is possible to hold the biological tissue M in a wide range and is possible to execute also the sandwiching of the biological tissue M, which is carried out in cooperation with the first electrode member 1, over a relatively wide range and the sandwiching operation becomes more certain. The sandwiching can be carried out reliably even in the case of various modes of foramen ovale valves M2 which are different depending on the person. Furthermore, as described in detail later on, there is also merit in that the fusion becomes relatively easy, also the fusion force is improved and it becomes difficult for a thrombus to attach.

The second electrode member 2 may be fixedly positioned with respect to the support body 50, but it is also possible to make it slidable so as to be retractable with respect to the support body 50. When it is position-fixed, the sticking to the foramen ovale valve M2 can be executed by moving the whole catheter 30 in the axial direction, but if it is freely movable in and out, the protruding length of the second electrode member 2 from the support body 50 can be adjusted, the surface area of the electrode area, which will be described in detail later on, can be adjusted comparatively easily, and also the supply of the electric energy can be adjusted. The surface area of the electrode surface does not include the area of the portion coated with an electrical insulation body or the like for the electrode, or the area of the electrode area housed in the catheter.

In order to employ a slidable construction, it is sufficient if the distal tip of the operation member 7b is mounted on the proximal side of the second electrode member 2 and a proximal end of the operation member 7b is connected with a knob 78b provided in the hand-operated operation unit 70. Then, when sliding this knob 78b in a reciprocating manner, it is possible to protrude and to move-backward the second electrode member 2 from the support body 50 through the operation member 7a.

Also, a conductive wire d2 is connected to the proximal side or end of the second electrode member 2, and the conductive wire d2 extends out to the outside from a Y connector 72 and is connected with the energy supply unit 20 through a coupler 77.

The support body 50 includes a plurality of lumens and it is also possible for them to be constructed by a plurality of catheters 30.

The support body 50 and the catheter 30 can be generically referred to as an attachment portion and this attachment portion is constituted by an electrical insulation member composed of a synthetic resin or the like. It is possible to employ a construction in which electric power supplied to the electrode members 1, 2 will not flow on the hand side or the like of the surgery operator.

In particular, there are applied various countermeasures for both the electrode members 1, 2 so as not to result in attachment of a thrombus and blood even if the electric energy is applied in the blood.

To explain these countermeasures, first a description is set forth about a state in which thrombi are attached to the electrode members 1, 2 which are applied with electric energy in the blood.

Consideration is given to the relationship between the fusion force with respect to electric energy and thrombus occurrence condition, and taking into account temperature conditions at respective portions of the biological tissue M when applying the electric energy.

Figure 7:
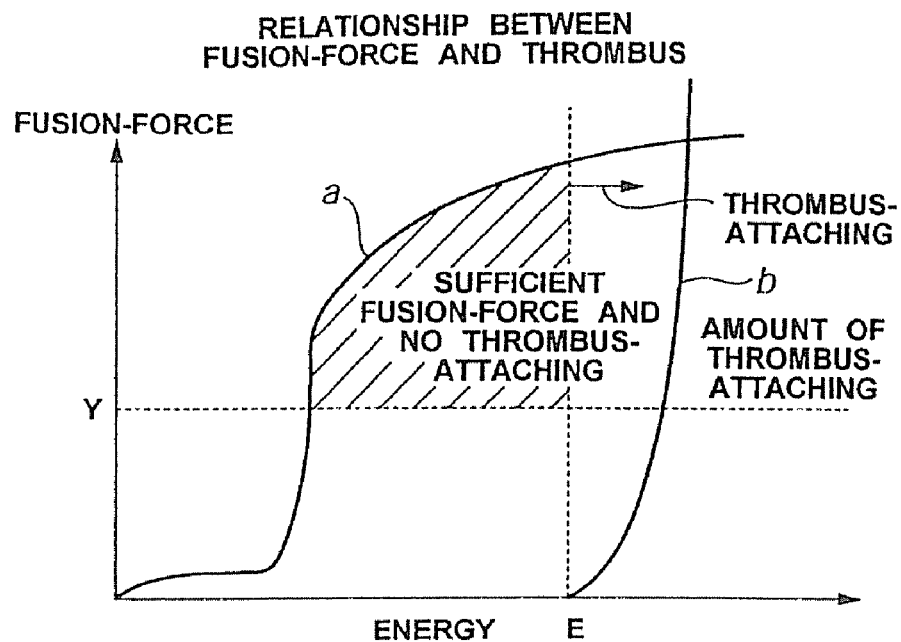
FIG. 7 is a graph showing the relationship between fusion force and thrombus-attaching with respect to electric energy.
Figure 8:
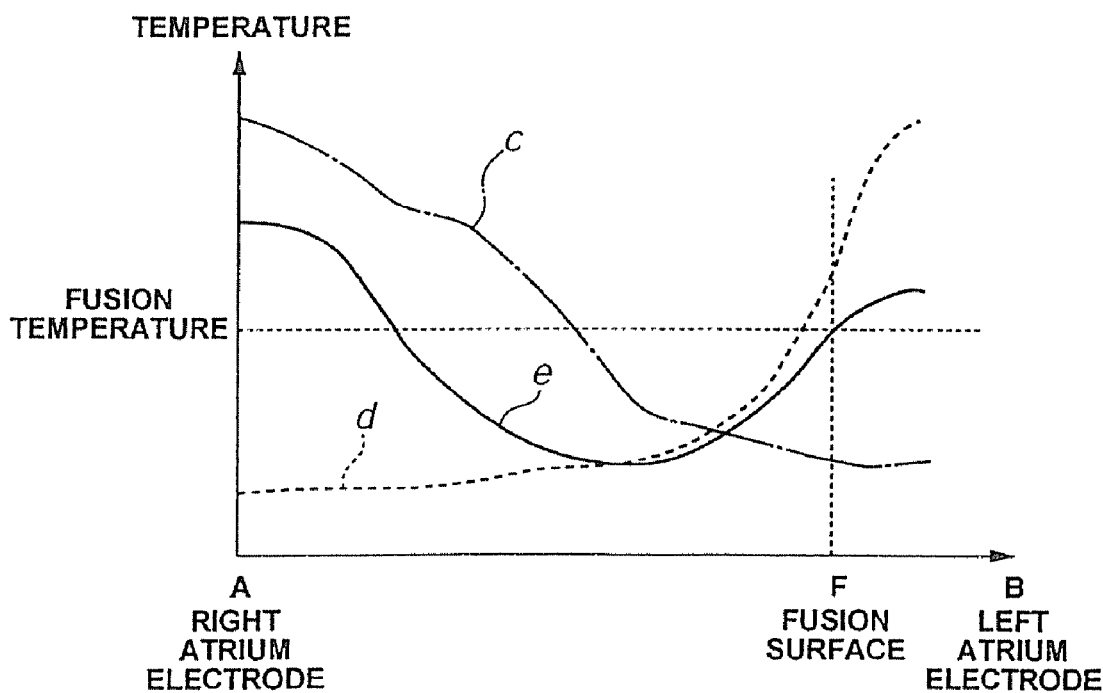
FIG. 8 is a graph showing a temperature condition in a case in which a biological tissue exists between A point corresponding to the one electrode member of FIG. 3 and point B corresponding to the other electrode member.

FIG. 7 is a graph showing the relationship between the fusion force and thrombus-attaching with respect to electric energy, and FIG. 8 is a graph showing temperature conditions in a case in which a biological tissue exists between point A corresponding to the first electrode member 1 of FIG. 4 and point B corresponding to the second electrode member 2.

In FIG. 3, the second electrode member 2 is stuck into the foramen ovale valve M2, and the first electrode member 1 is attached on or held against the atrial septum M1. Thereafter, when electric energy is applied in a state in which the atrial septum M1 and the foramen ovale valve M2 are sandwiched by the second electrode member 2 positioned on the left atrium side and the first electrode member 1 positioned on the right atrium side, generally, as shown by a solid line a in FIG. 7, the fusion force of the biological tissue increases along with the increase of the electric energy. As shown by a solid line b in FIG. 7, the amount of thrombus-attaching increases rapidly from a point of a certain amount of electric energy (E). Consequently, in order to obtain a predetermined fusion force (Y) without attachment of the thrombus, the electric energy is to be controlled by aiming for the shaded area in FIG. 7.

The temperature state of each region when the electric energy is applied to the first electrode member 1 and the second electrode member 2 sandwiching the biological tissue has a tendency shown by a broken line d in FIG. 8 in a case in which the surface area of the first electrode member 1 on the right atrium side (proximal side) is larger than the surface area of the second electrode member 2 on the left atrium side (distal side). On the contrary, in a case in which the surface area of the electrode member on the right atrium side (proximal side) is smaller than the surface area of the electrode member on the left atrium side (distal side), the tendency will be as shown by an alternate long and short dash line c. Therefore, in order to secure a predetermined fusion force on the fusion surface F, it is preferable to adjust the electric energy and to control the temperature such that the fusion surface F reaches a temperature by which the tissue is adequately fused and at the same time, such that it reaches a tendency shown by the solid line e which shows a state in which a thrombus is not attached to the second electrode member 2 on the left atrium side (distal side) either.

Consequently, a first countermeasure is to adjust the electric energy which both the electrode members 1, 2 supply to the biological tissue and more specifically, to adjust the surface areas of the first electrode member 1 which is a plate-shaped electrode member and of the second electrode member 2 which is a pair of needle-shaped electrode members.

In particular, it is necessary for the second electrode member 2, which is a needle-shaped electrode member according to this disclosed embodiment, to have a predetermined area for the sandwiching of the biological tissue, but actually the surface area becomes smaller and the electric energy per unit area thereof becomes larger compared with those of the first electrode member 1 which is a plate-shaped electrode member, and a so-called energy concentration occurs easily and also the thrombus will attach easily. Furthermore, it is positioned on the left atrium side, which is the downstream side of the blood flow, and so there is a fear that the thrombus will flow stream to an undesirable position such as a peripheral blood vessel of the brain or the like. It is also a portion in which the thrombus-attaching should desirably be reliably prevented.

Consequently, in this embodiment, the first electrode member 1 is coated with an electrical insulation body Z such that the entire surface area of the portion in which the first electrode member 1 functions as an electrode (hereinafter referred to as electrode area or electrode surface area) is smaller than the entire surface area of the portion in which the second electrode member 2 functions as an electrode (hereinafter referred to as electrode area or electrode surface area). The electric energy which both the electrode members 1, 2 supply to the biological tissue is adjusted, and the electric energy concentration on one electrode member is avoided.

Figure 5:
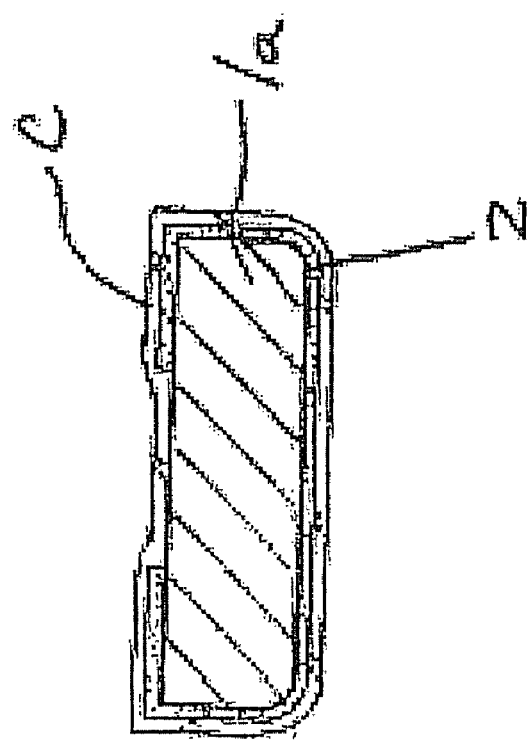
FIG. 5 is a cross-section view of the damper along the section line 5-5 in FIG. 4.

More specifically, as shown in FIG. 4 and FIG. 5, a portion of the ventral surface side of the main body portion 1a in the first electrode member 1, which contacts the biological tissue M, is coated with the electrical insulation body Z, and further the back surface side which does not contact the biological tissue M is coated with the electrical insulation body Z. With this construction, the surface area of the electrode surface of the first electrode member 1 is adjusted and the thrombus-attaching with respect to the second electrode member 2 is prevented.

Here, it is possible for the electrical insulation body Z coated on the back surface side of the main body portion 1a to be diamond-like-carbon (DLC), silicone, poly-ether-ethter-ketone (Peek), polycarbonate, poly-para-xylylene, urethane, polyetherimide, polyethersulphone (PES) and the like. These have favorable properties in electrical insulation, heat resistance, abrasion quality, sliding property and corrosion resistance.

In order to adjust the electric energy supply of the electrode members 1, 2, it is possible to apply the coating to the portion contacting the biological tissue M with the electrical insulation body Z as mentioned above and in addition, it is also possible to adjust the surface areas of the electrode surfaces of both the electrode members 1, 2 and to coat only the side of the first electrode member 1 which does not contact the biological tissue with the electrical insulation body Z. In this manner, if the portion, which does not contact the biological tissue M, of at least one of the electrode members 1 or 2, is coated with an electrical insulation body, it is possible to restrict the region to which the respective electrode members 1, 2 can supply electric energy with respect to the biological tissue M, so that it does not happen that the temperature increases even for the unnecessary portions of the biological tissue M and it is possible to prevent occurrence of such a problem that a thrombus will be attached by coagulating the blood which flows in the periphery of the respective electrode members 1, 2.

Specifically, the foramen ovale valve M2 is a membrane of around 1 mm and is easily broken, and moreover, it is a portion which will receive the influence of the temperature increase caused by the fine second electrode member 2 contacting therewith. On an occasion of applying treatment with respect to such a portion, when the surface areas S1, S2 of the electrode surfaces of both the electrode members 1, 2 are adjusted and the electric energy supply is adjusted, the electric energy concentration can be avoided in the respective electrode members 1, 2 and accordingly, it is possible to perform a procedure while controlling the temperature increase of the biological tissue in the vicinity of the respective electrode members without the attachment of a thrombus to any one of the electrode members and moreover without a phenomenon in which only the vicinity of either one of the electrode member sides becomes high in temperature earlier, so that it becomes possible also for the procedure to be performed more easily.

A second countermeasure for avoiding attachment of a thrombus and blood even if the electric energy is applied in the blood involves applying a coating as an electrical insulation body such that the area (S1) of the electrode surface of the first electrode member 1 on the right atrium side becomes smaller than the area (S2) of the electrode surface of the second electrode member 2 on the left atrium side.

Upon using this medical device, the blood on the right atrium side in which the first electrode member 1 is arranged is sent to a lung from a pulmonary artery, and the blood on the left atrium side in which the second electrode member 2 is arranged is sent to the whole body from the aorta. More specifically, with respect to the blood on the left atrium side, the blood is sent also to the brain. For this reason, when a thrombus is formed on the left atrium side, there is a fear that the thrombus will reach the brain and will embolize the brain blood vessel, and so thrombus formation on the left atrium side owing to the use of this medical device should be avoided.

In the present embodiment, the concentration of energy at the electrode member 1 on the left atrium side and the possibility of thrombus formation is avoided by forming the area S1 of the electrode surface of the first electrode member 1 on the right atrium side to be smaller than the area S2 of the electrode surface of the second electrode member 2 on the left atrium side (S1<S2).

As a specific example for establishing this relationship (S1<S2), it is possible to coat the first electrode member 1 with an electrical insulation film so that the area of the electrode surface of the first electrode member 1 is smaller than the area S2 of the electrode surface of the second electrode member 2. In addition, it is also possible to form or configure the area S2 of the electrode surface of the second electrode member 2 to be smaller than the area S1 of the electrode surface of the first electrode member 1 by constructing the plurality of second electrode members 2 protruding from the support body 50 to be movable forward and backward by the operation member 7b and by adjusting the protruding length from the support body 50. More specifically, as shown in FIGS. 3 and 4, it is possible that the proximal side of the second electrode member 2 is coated with the electrical insulation body Z so that an electrode area represented by the exposed distal portion over a predetermined length h is formed. With this construction, it is possible, by only adjusting the protruding length from the attachment portion of the electrode member 2, to change the electric energy supply relatively easily and convent, and readiness or the like of the procedure is improved.

Here, upon adjusting the supply of electric energy, it is verified by experiments about the area ratio (S1/S2) between the surface area (S2) of the electrode surface of the second electrode member 2 and the surface area (S1) of the electrode surface of the first electrode member 1.

It should be noted that the wording "surface area of electrode surface" does not include the area of the portion coated with an electrical insulation body or the like for the electrode, or the area of the electrode area housed in the catheter.

For an experiment, various combinations of a first electrode member 1 and second electrode member 2 are prepared in which the aforesaid surface area ratios (S1/S2) are 0.5, 0.6, 0.7, 0.8, 0.9 and 1.0. In each case, the first electrode member 1 is a plate-shaped electrode member and the second electrode member 2 is a needle-shaped electrode member. An atrial septum M1 and a foramen ovale valve M2 of a pig's heart are used and in a state in which these are soaked in the blood, the second electrode member 2 is stuck into the foramen ovale valve M2 and the first electrode member 1 is contacted with the atrial septum M1. An experiment was performed involving energization by an output power of 15 W for a predetermined time period. There was obtained a result shown in the following Table 1.

TABLE 1

| area ratio | thrombus-attaching to second electrode member | fusion |
|---|---|---|
| 1 | YES | YES |
| 0.9 | NO | YES |
| 0.8 | NO | YES |
| 0.7 | NO | YES |
| 0.6 | NO | YES |
| 0.5 | NO | NO |

As is clear from this table, the aimed fusion force was not obtained for a case in which the surface area ratio (S1/S2) is 0.5, the aimed fusion force was obtained in case of the surface area ratio or at least 0.6, and there existed attachment of an unfavorable thrombus in case of 1.0.

Consequently, if the area ratio (S1/S2) of the surface of both the electrode members is more than 0.6 to less than 1.0, thrombus attachment can be prevented at the same time as fusion is achieved.

The aforesaid experiment shows a situation in which the output energization is 15 W. The results shown in the following Table 2 were obtained after carrying out an experiment similar to that described above, except that the energization which is performed for a predetermined time period is performed with the energization output varying, while using a fixed area ratio (S1/S2) of 0.7.

TABLE 2

| Output (W) | thrombus-attaching to second electrode member | fusion |
| --- | --- | --- |
| 10 | NO | YES |
| 15 | NO | YES |
| 20 | NO | YES |
| 30 | NO | YES |
| 50 | NO | YES |

The results summarized in this table show that thrombus attachment to the second electrode member 2 of the left atrium did not occur in a range of 10 W to 50 W and the desired fusion force was obtained. Therefore, it is clear that it is sufficient for the energization output to be in a range of 10 W to 50 W.

Even in the case of such electrode members 1, 2, if a coating layer C is further formed by applying a coating, plating or the like on the surfaces of the respective electrode members 1, 2 (whole ventral surface side of the first electrode member 1 and whole surface for the second electrode member 2) by using an electrically-conductive material to which a biological tissue and a thrombus or blood are not attached, an attachment preventing effect of the tissue and the electrode can be obtained and it becomes more desirable.

Examples of such an electrically-conductive material for the coating include titanium nitride (TiN), titanium carbonnitride (TiCN), chromium nitride, aluminum nitride, PTFE+ nickel, PTFE+gold, platinum, silver, carbon black and the like. These materials have characteristics such that, for example, the tissue is not scorched; electrical conductivity is very good; abrasion quality, sliding property, corrosion resistance and heat resistance are favorable; and so that they are desirable.

Figure 9:
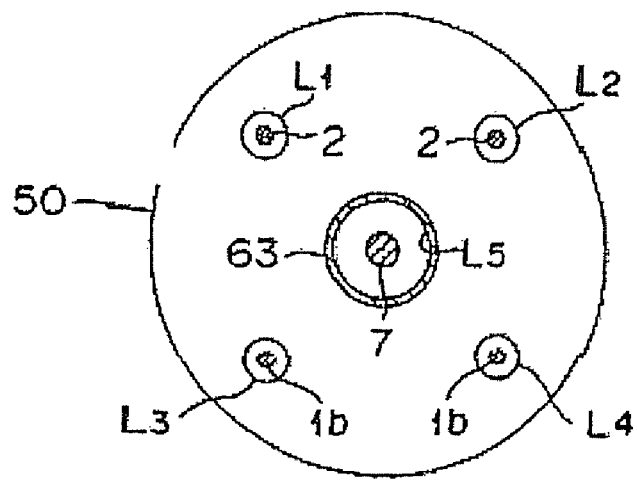
FIG. 9 is a cross-sectional view of the medical device taken along the section line 9-9 line in FIG. 2.

FIG. 9 illustrates the support body shown in FIG. 2 in cross-section. The support body 50 is position-fixed at the distal portion in the catheter 30, and five lumens L1 to L5 are provided in the support body 50 as shown in FIG. 9.

The second electrode member 2 and the first electrode member 1 mentioned above are positioned in the first and second lumens L1, L2 and the third and fourth lumens L3, L4. The positioning hold mechanism 60 is provided in the fifth lumen L5 which is centrally positioned in the support body 50 and possesses the maximum aperture size (e.g., greatest diameter). Here, it is not always necessary for the support body 50 to be provided as a separate body with respect to the catheter 30, and it is also possible to use the catheter 30 (multiple-lumen catheter) in which a plurality of lumens are formed inside.

The positioning hold mechanism 60, as shown in FIG. 2, generally, includes a positioning portion 61 for positioning the second electrode member 2 with respect to a foramen ovale o and a holding portion 62 for holding the foramen ovale valve M2 with respect to the sticking direction of the second electrode member 2 so as not to allow the backward movement thereof, and normally it is housed in the guiding catheter 31, but it is pushed out from the guiding catheter 31 by the operation member 7 upon use.

To describe in more detail, in the center lumen L5 is provided a main tube 63 for reinforcing the catheter 30 and for pulling and withdrawing the positioning hold mechanism 60 in/from the catheter 30; an operation member 7 which is provided to move forward and backward freely in the axial direction in the main tube 63 and operates the positioning hold mechanism 60; a positioning portion 61 which is operated by the operation member 7 to effect expansion and contraction thereof and which is composed of a pair of first elastic wires 66 connecting the main tube 63 with a middle sleeve body 64; and the holding portion 62 which includes a bump member 68 provided at the distal portion of the operation member 7, a distal sleeve body 65, and a pair of second elastic wires 67 connecting the middle sleeve body 64 with the distal sleeve body 65 and adapted to hold the foramen ovale valve M2 by the bump member 68 and the distal sleeve body 65.

With respect to the positioning portion 61, the operation member 7 protrudes from the distal tip of the main tube 63, the first elastic members 66 are displaced outward by moving the operation member 7 forward and backward in the axial direction, respective first elastic members 66 press the inner fringe of the foramen ovale o with approximately equal elastic forces, and the second electrode member 2 is center-aligned with respect to the foramen ovale o. In other words, the positioning portion operates to position the second electrode member 2 which is positioned between both the first elastic members at the center portion of the foramen ovale o.

The holding portion 62 includes a bending mechanism W for bending the distal portion of the operation member 7 by operating the operation member 7 in the axial direction so as to move forward and backward. The bending mechanism W bends the holding portion 62 so that the holding portion faces the direction in which the second electrode member 2 sticks the foramen ovale valve M2 and operates to hold the foramen ovale valve M2. Here, the bending mechanism W is constituted by the middle sleeve body 64, the distal sleeve body 65, the second elastic wire 67 for coupling both the sleeve bodies 64, 65 and the bump member 68.

The proximal tip of the first elastic wire 66 is secured (e.g., welded) on the distal tip of the main tube 63, and the distal side of the first elastic wire 66 is secured (e.g., welded) on the middle sleeve body 64. The proximal tip of the second elastic wire 67 is secured (e.g., welded) on the distal tip of the middle sleeve body 64 and the distal side of the second elastic wire 67 is secured (e.g., welded) on the distal sleeve body 65.

Preferable examples of materials for the first and second elastic wires 66, 67 include metallic wire such as stainless steel, nickel-titanium, super elastic alloy (for example, Ni—Ti alloy) and the like with an outer diameter of around 0.1 mm to 0.5 mm. It is also possible to prevent the tissue from being wounded by coating a metallic wire with a (soft) resin tube.

The holding portion 62 has a construction in which the first elastic wire 66 of the proximal side bends prior to the second elastic wire 67 of the distal side; the positioning of the second electrode member 2 is executed; subsequently, the operation member 7 itself is deformed accompanied by the bump member 68 and the distal sleeve body 65; and the positioning portion 61 holds the foramen ovale valve M2 after positioning the second electrode member 2.

With respect to this construction, for example, it is also possible to use a method in which the second elastic wire 67 has a higher material stiffness than that of the first elastic wire 66; and a method in which an easily-deformable portion is formed by bending a portion of the first elastic wire 66 beforehand or the like and when the moving or pulling force is applied, the first elastic wire 66 is bent previously compared with the second elastic wire 67 by the deformation of the easily-deformable portion.

When operating in this manner, the first elastic wire 66 of the proximal side is attached to the inner fringe of the foramen ovale o only by moving or pulling the operation member 7 backward, and so the positioning of the second electrode member 2 can be executed. Upon applying further movement (pulling back), the second elastic wire 67 of the distal side protrudes and is deformed like an arc shape toward the outward radial direction and it is possible to hold the foramen ovale valve M2 so as not to allow the backward movement thereof such that it becomes easy for the second electrode member 2 to be stuck.

Figure 10:
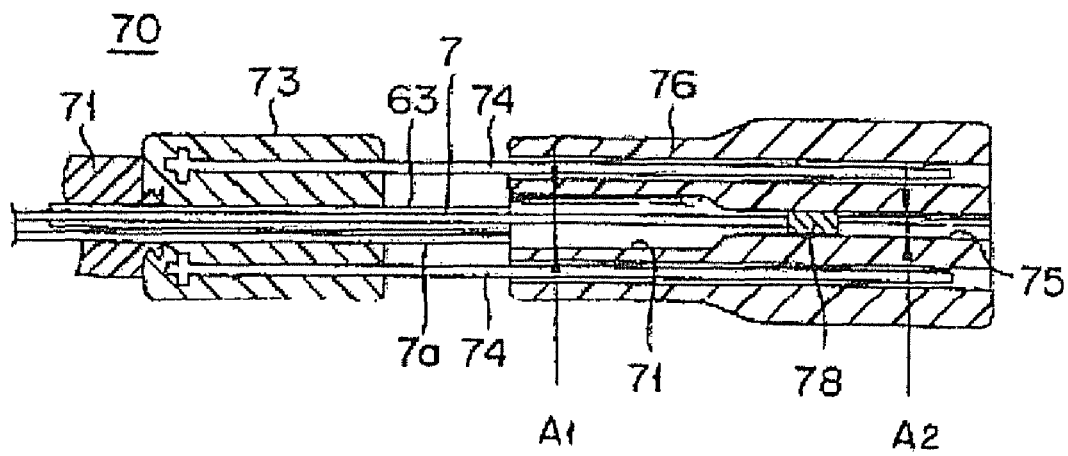
FIG. 10 is a cross-sectional plan view of an operation unit of the medical device.

FIG. 10 is a cross-section plan view of the operation unit of the medical device. The operation unit 70 generally includes a first operation body 73 with which the proximal tip of the catheter 30 is coupled through a coupling member 71 and a Y connector 72, and a second operation body 76 movable towards and away from the first operation body 73 by sliding along slide rails 74. The first operation body 73 includes respective holes in which are positioned the slide rails 74 that protrude from the rear end side of the first operation body 73.

The main tube 63 is positioned in the inside of the first operation body 73 and the rear end of the main tube 63 is coupled to the distal tip of the second operation body 76. Consequently, when applying backward movement or force on the second operation body 76, it is possible to withdraw the whole positioning hold mechanism 60 within the center lumen L5 of the catheter 30. Examples of materials which can be sued for the main tube 63 include a deformable elastic material such as, for example, polyimide resin, polyurethane, PET, nylon, fluorine resin, polypropylene and the like. In addition, it is also possible to make the operation unit 70 as a metallic pipe and to couple it with the main tube 63 of an elastic material.

With respect to the operation member 7, the proximal tip thereof is mounted on a knob 78 which slides reciprocatingly in a slide groove 75 formed in the center of the second operation body 76. When the knob 78 is slid reciprocatingly in the slide groove 75, the whole operation member 7 moves in a reciprocating manner in the main tube 63.

As shown in FIG. 10, the slide groove 75 includes a front portion (front half portion) having a broader (greater) width A1 than the width A2 of the rear portion (rear half portion). Thus, in a case in which the knob 78 is positioned at the front half of the slide groove 75, it is possible to move (rotate) the knob 78 in a tilting manner in a direction perpendicular to the axial line of the slide groove 75 (i.e., it is possible to move the knob 78 laterally or side-to-side) and thus, it is possible to rotate the operation member 7 in the catheter 30 in a manner centered on the axial line and to rotatingly adjust the distal tip position. Consequently, when the operation member 7 is operated by operating the knob 78, it is possible to adjust not only the position in the forward and backward direction, but also the rotational position. Thus, the convenience of the procedure for inserting into the left atrium is improved considerably.

The operation member 7a is a member for moving the plate-shaped first electrode member 1 forward and backward. Thus, in this embodiment, the proximal side thereof is coupled to the distal portion of the second operation body 76.

On the other hand, the operation member 7b is a member for moving the needle-shaped second electrode member 2 forward and backward, and the proximal side thereof is inserted into the inside of the main tube 63 and is coupled to the knob 78b which slides reciprocatingly in a sub-slide groove 75b formed in the first operation body 73.

It should be noted, in a case in which the first electrode member 1 and the second electrode member 2 are respectively operated individually, that it is also possible for the operation member 7a to be connected to a knob 78a which slides reciprocatingly in a sub slide groove 75a formed in the first operation body 73 (shown by alternate long and short dash line) so as to move forward and backward.

The energy supply unit 20 is an electrical unit as mentioned above and it is possible for the energy supply method to use a method such as a monopolar system in which the second electrode member 2 on the left atrium L side is an active electrode and is energized with respect to a counterpart electrode plate provided at the back portion, a monopolar system in which the first electrode member 1 on the right atrium R side and the second electrode member 2 on the left atrium L side are active electrodes and are energized with respect to counterpart electrode plates provided at the back portion, a bipolar system in which energization is executed between the first electrode member 1 on the right atrium R side and the second electrode member 2 on the left atrium L side. In particular, if it is formed as a bipolar system for controlling the current by the impedance of the biological tissue between the first electrode member 1 and the second electrode member 2, there are advantages that it can have correspondence relatively easily in response to the state of the tissues of the foramen ovale valve M2 and the atrial septum M1 which differ depending on a person. Thus, safety and convenience of the procedure can be obtained.

The power supply unit 20A is constituted by a power supply, a control unit for controlling current and the like, and a well-known system can be employed so that a detailed explanation thereof will not be set forth. Here, it is not necessary to employ a direct-current power supply for the power supply as it is also possible to employ an alternative-current power supply.

The operation of the present medical device described above is as follows.

FIG. 11A to FIG. 11D schematically show operation states of the medical device. It should be noted in the drawings that the shape and position of the second elastic wire member 66 are in a state of being approximately the same plane as those of the first electrode member 1 and the second electrode member 2, but in order to facilitate an understanding, the drawn position thereof is shown in a state being displaced by 90° and is different from the actual deformed state.

First, the surgery operator moves the second operation body 76 of the hand-operated operation unit 70 backward with respect to the first operation body 73 so that the first electrode member 1, the second electrode member 2 and the like are housed in the guiding catheter 31. The distal tip of the guiding catheter 31 is inserted from a predetermined position of the living body by using a guide wire as a guide until it reaches the right atrium R by passing through the inferior vena cave J. Here, it is also possible to insert only the guiding catheter 31 into the living body and afterward to insert the catheter 30 by using the guiding catheter 31 as a guide.

Figure 11:
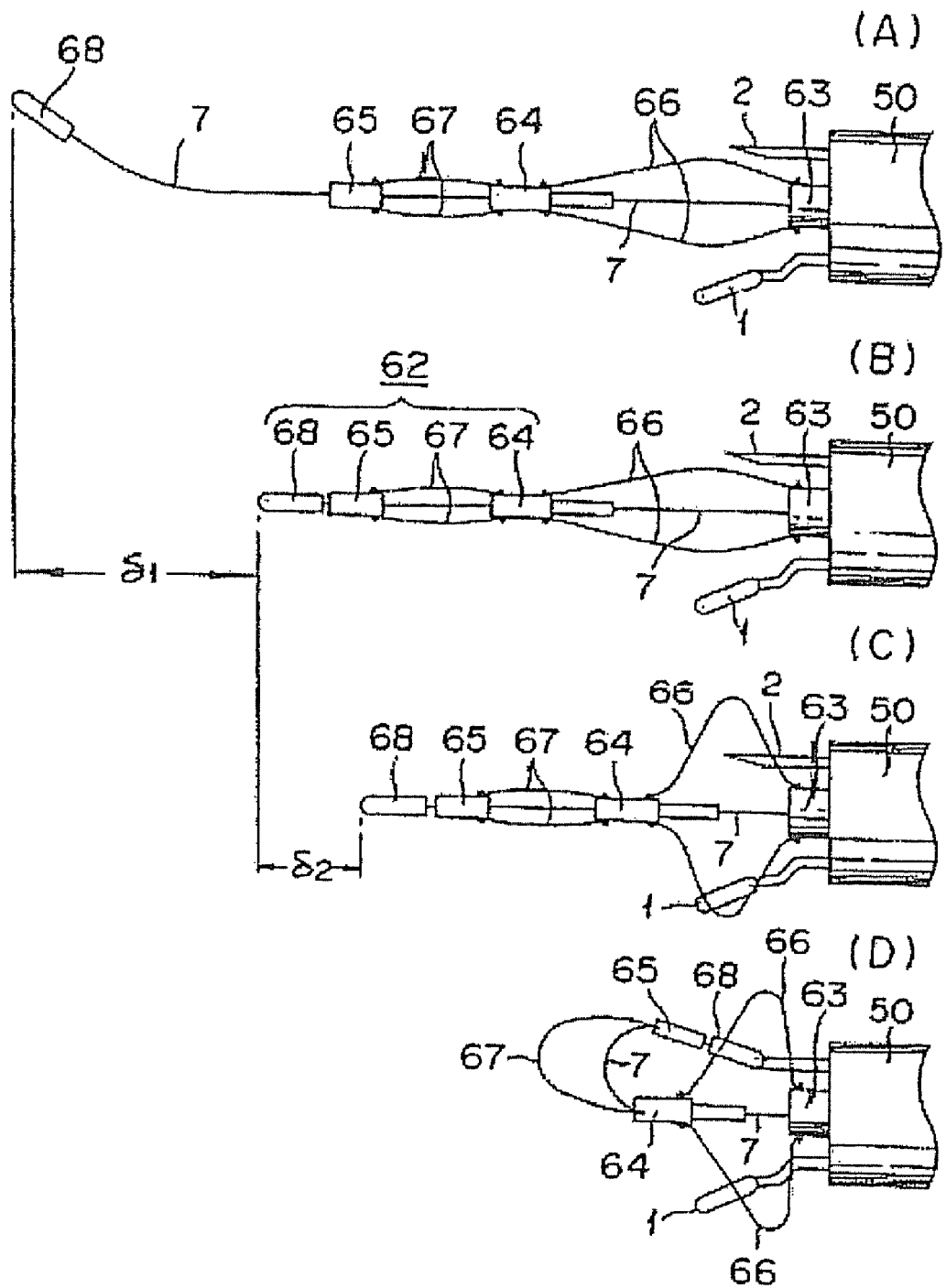
FIGS. 11A-11D are schematic views showing operation states of the medical device.

Next, the first operation body 73 is operated and the distal tip of the catheter 30 is protruded to the left atrium L from the right atrium R through the foramen ovale o. Thereafter, the knob 78 is moved forward and, as shown in FIG. 11A, the distal tip of the operation member 7 is moved forward to protrude from the distal sleeve body 65 and is inserted into the left atrium L. It is possible to visually observe this protruding state from the outside if a marker is provided on the bump member 68 or the like. It is also possible to identify, by feel, a general place at which the distal tip of the operation member 7 is positioned when the distal tip of the operation member 7 bumps the inner wall of the left atrium L or the like, for example in a situation where it may be difficult to visually observe by eyes, so that the convenience is improved. The knob 78 is positioned at the wide front half portion of the slide groove 75 and when this knob is moved in a tilting manner, the identification of the distal position becomes more easily sensitive.

After identifying the distal position of the operation member 7, the knob 78 is moved backward as shown in FIG. 11B until the bump member 68 of the operation member 7 contacts the distal sleeve body 65 (amount of backward movement is indicated by δ1 in FIG. 11B). Then, the first operation body 73 is operated, and the second elastic wire 67, the first electrode member 1 and the second electrode member 2 are positioned in the vicinity of the foramen ovale valve M2 and the whole holding portion 62 is inserted into the left atrium L side.

When the knob 78 is further moved backward (amount of backward movement is indicated as δ2 in FIG. 11C), the operation force for the backward movement is transmitted by the operation member 7 to the first elastic wire 66 firmly fixed on the distal tip of the main tube 63 through the bump member 68, the distal sleeve body 65, the second elastic wire 67 and the middle sleeve body 64. The first elastic wire 66 is, as shown in FIG. 11C, outwardly deformed in an arc shape toward the outside direction (in the radially outward direction). However, at this point in time, the second elastic wire 67 is not deformed.

As the first elastic wire 66 is outwardly deformed, it pushes on and widens the opening edge portion of the foramen ovale o so that the second electrode member 2 which is provided in close vicinity of the first elastic wire 66 is center-aligned with respect to the foramen ovale o and the second electrode member 2 is positioned at the center of the foramen ovale o.

When the knob 78 is further operated to move backward until the rear end of the middle sleeve body 64 contacts the distal tip of the main tube 63, as shown in FIG. 11D, the first elastic wire 66 is not additionally deformed so much, but the second elastic wire 67 of the distal side protrudes and deforms in an arc shape toward the outside direction in the radial direction by the aforementioned operation force. Consequently, in the left atrium L, the bump member 68 and the distal sleeve body 65 approach the second electrode member 2, so that the bump member 68 and the distal sleeve body 65 contact the surface of the left atrium side of the foramen ovale valve M2 and hold this.

In this state, when the first operation body 73 is moved forward or the knob 78a is moved forward in the sub slide groove 75a, the first electrode member 1 moves or protrudes from the distal tip of the catheter 30. Also, when the knob 78b is moved forward in the sub slide groove 75b, the second electrode member 2 which is provided at the distal tip of the catheter 30 protrudes or moves and is stuck at a predetermined position of the foramen ovale valve M2. In particular, the second electrode member 2 of the present embodiment is expanded at the distal tip thereof, so that the sticking is executed at two places spaced apart from each other, the position fixing is attained for the relationship with respect to the foramen ovale valve M2, and also the device itself is stabilized positionally. The sticking state is the state shown in FIG. 1 and is a state in which the atrial septum M1 and the foramen ovale valve M2 exist or are positioned between the first electrode member 1 and the second electrode member 2.

When the sticking is completed, the second operation body 76 is returned and, as shown in FIG. 11B, the first elastic wire 66 and the second elastic wire 67 return to a straight-line shape and thereafter, the second operation body 76 is operated to move backward and the whole positioning hold mechanism 60 is withdrawn in the lumen L5 of the catheter 30 by the main tube 63.

At the time of this withdrawal, the operation member 7a of the first electrode member 1 coupled to the second operation body 76 also moves backward along the lumen of the catheter 30, so that a bend portion f of the first electrode member 1 is deformed so as to approach the side of the second electrode member 2 by the end portion of the catheter 30 and the atrial septum M1 and the foramen ovale valve M2 are strongly sandwiched between both the electrode members 1, 2.

It should be noted that in a case in which the first electrode member 1 and the second electrode member 2 are to be operated individually respectively, the knob 78a is moved backward in the sub slide groove 75a. In this manner, it will become possible to sandwich the atrial septum M1 and the foramen ovale valve M2 between both the electrode members 1, 2 and this fact is similar as the case in which the operation member 7a of the first electrode member 1 is coupled to the second operation body 76.

When electric current of 15 W to 50 W is applied between the first electrode member 1 and the second electrode member 2 while maintaining this sandwiched state, it is possible to supply electric energy to the biological tissue from the electrode surfaces of the respective electrode members 1, 2 which were made to have predetermined surface areas by the electrical insulation body Z, whereupon the biological tissue in the vicinity of or in contact with the respective electrode members 1, 2 are heated.

Also, the electric energy is controlled such that a thrombus caused by coagulation of the blood flowing at the periphery of the respective electrode members 1, 2 is not generated. Thus, even if a portion of both electrode members 1, 2 is exposed in the blood, the attachment of the thrombus to that portion does not occur. Moreover, owing to a fact that the surfaces of the electrode members are plated, the attachment of the thrombus to the respective electrode members is more reliably prevented.

When both the tissues of the atrial septum M1 and the foramen ovale valve M2 are heated in this manner, the tissues of the foramen ovale valve M2 and the atrial septum M1 melt and are mutually fused by an adhesive agent such as collagen, erastin and the like.

When the fusion is completed, the energization is stopped, the second operation body 76 is moved backward, also the first electrode member 1 and the second electrode member 2 which are located at the distal tip of the catheter 30 are housed in the guiding catheter 31 together with the positioning hold mechanism 60, and the guiding catheter 31 is pulled out from the living body. The very small hole remaining on the foramen ovale valve M2 by the pulling-out of the first electrode member 1 will heal afterward and a bad influence such as generation of a thrombus or the like is not likely to occur.

The medical device and its manner of operation are not limited by embodiment described above, and it is possible for a person skilled in the art to employ various modifications within the technical concept of the disclosure here.

For example, the medical device described above is used for closing the defect of the PFO, but the present invention is not limited only to this usage as it has high versatility. The medical device here can be used also in the case of closing a defect such as an atrial septum defect (ASD), a PFO, a ventricular septal defect (VSD), a patent ductus arteriosus (PDA) and the like. In addition, it can also be used to close a passway-shaped defect such as a left auricle closing device (Left Atrial Appendage) or in case of thermally necrosing a biological tissue in a predetermined region. In particular, foreign substances are not indwelled in the body, the construction is relatively simple, the procedure is relatively easy and it is possible to suture the foramen ovale valve and the atrial septum quite reliably.

For example, the procedure for closing a congenital atrial septum defect (ASD) can be as follows. First, similar to the case of closing a PFO, a device including a damper K which is installed in the percutaneous catheter 30 is entered into the body from the inferior vena cave. After the entering, a needle-shaped electrode member 2 is stuck to a biological tissue at a periphery of an atrial septum defect. After this sticking, the middle-region portion from the distal portion of the needle-shaped electrode member 2 is exposed in the left atrium beyond the atrial septum. In addition, the other plate-shaped electrode member 1 does not go beyond the atrial septum and is arranged at the periphery of the atrial septum defect region on the right atrium side. After this arrangement, the biological tissue at the periphery of the atrial septum defect region is sandwiched and pressed by both the electrodes on the right atrium side and on the left atrium side and thereafter, the biological tissue is fused by applying electric energy and the atrial septum defect is closed.

Even in a case in which it is hard to sandwich a biological tissue at a periphery of a defect such as in a case of an atrial septum defect or the like, it becomes sandwichable by both the electrode members comparatively easily when displacing the biological tissue directed to the other plate-shaped electrode member 1 after executing the sticking by the needle-shaped electrode member 2.

Also, when arranging one electrode member beyond the biological tissue and arranging the other electrode member on the front side of the biological tissue in this manner and when the area (S3) of the electrode surface of the needle-shaped electrode member is larger than the area (S4) of the electrode surface of aforesaid other electrode member in such a case in which the blood flow is directed from the other electrode member side on the front side to the aforesaid needle-shaped electrode member side, an effect occurs that it becomes difficult for the thrombus to be attached to the downstream side of the flow and so thrombus attachment is not likely to occur. If the area ratio (S4/S3) of these electrode areas is more than 0.6 to less than 1.0, in a manner similar to that described previously, it becomes difficult for both the electrode members to be attached with a thrombus and the procedure becomes easier.

With respect to the device of the aforesaid exemplary embodiment, it is merely housed in the catheter and operates as a sandwich mechanism by the operation member, but it is not limited to this. For example, it is also possible to carry it to a predetermined position by employing a combination with a so-called catheter having a balloon.

The device disclosed here is utilized as a medical device by which a defect portion such as a PFO and the like is closable in a relatively simple manner and also quite safely.

Having described preferred embodiments of the medical device with reference to the accompanying drawings, it is to be understood that the invention is not limited to those precise embodiments and that various changes and modifications may be made by others, and equivalents employed, by one skilled in the art without departing from the spirit or scope of the invention as defined in the appended claims.

What is claimed is:

1. A method for fusing a biological tissue, comprising:
positioning a first electrode member on one side of biological tissue, the first electrode member comprising a flat plate-shaped electrode member defining a first electrode surface possessing an electrode surface area;
providing a second electrode member comprising a pair of needle-shaped electrode members defining a second electrode surface possessing an electrode surface area that is different from the electrode surface area of the first electrode surface;
sticking an opposite side of biological tissue with the pair of needle-shaped electrode members; and
supplying electric energy between the first electrode surface and the second electrode surface while the biological tissue is sandwiched between the first electrode surface and the second electrode surface to fuse the biological tissue;
wherein the first electrode includes a coated portion that is coated with an electrical insulation member and an exposed portion that is not coated with an electrical insulation member, the exposed portion defining the entire conductive electrode surface (S1) of the first electrode member;
wherein the needle-shaped electrode members defining the entire conductive electrode surface (S2) of the second electrode member; and
wherein a ratio (S1/S2) between the entire conductive electrode surface area (S1) of the first electrode member and the entire conductive electrode surface area (S2) of the second electrode member comprising the pair of needle-shaped electrode members is more than 0.6 and less than 1.0.

2. The method according to claim 1, wherein the biological tissue comprises foramen ovale valve and atrial septum, and the method further comprises sticking the foramen ovale valve with the pair of needle-shaped electrode members, and sandwiching the foramen ovale valve and the atrial septum between the pair of needle-shaped electrode members and the first electrode member.

3. The method according to claim 1, wherein the energy supply unit comprises a bipolar system controlling current by impedance of the biological tissue between the two electrode members.

4. The method according to claim 1, wherein the pair of needle-shaped electrode members are configured to diverge away from one another in a direction toward a distal end of the needle shaped electrode members from a proximal end of the needle-shaped electrode members.

5. The method according to claim 1, wherein a portion of a ventral surface side of the first electrode is coated with an electrical insulation member.

6. A medical device for fusing a biological tissue, comprising:
a first electrode member possessing a size positionable in a living body on one side of biological tissue;
a second electrode member possessing a size positionable in the living body on an opposite side of the biological tissue;
an energy supply unit configured to supply electric energy to between the first and second electrode members;
the first electrode member comprising a flat plate-shaped electrode member possessing an electrode surface, the first electrode member being positionable in the living body so that the electrode surface of the first electrode member is positioned on a front side of the biological tissue;
the second electrode member comprising a pair of needle-shaped electrode members configured to stick the biological tissue so that the pair of needle-shaped electrode members extend from the front side of the biological tissue through the biological tissue to a side of the biological tissue opposite the front side of the biological tissue;

the pair of needle-shaped electrode members possessing an electrode surface, the pair of needle-shaped electrode members being positionable in the living body so that the electrode surface of the pair of needle-shaped electrode members is positioned beyond the biological tissue by the sticking of the biological tissue; and the electrode surface of the first electrode member possessing a first conductive electrode surface area (S1), and the electrode surface of the pair of needle-shaped electrode members possessing a second conductive electrode surface area (S2);

wherein the first conductive electrode surface area (S1) defines the entire conductive electrode surface of the first electrode member and the second conductive electrode surface area (S2) defines the entire conductive electrode surface of the pair of needle-shaped electrode members;

wherein the ratio (S1/S2) between the first conductive electrode surface area (S1) and the second conductive electrode surface area (S2) is more than 0.6 and less than 1.0; and wherein the pair of needle-shaped electrode members are configured to diverge away from one another in a direction toward a distal end of the needle shaped electrode members from a proximal end of the needle-shaped electrode members.

7. The medical device according to claim 6, wherein a portion of a ventral surface side of the first electrode is coated with an electrical insulation member.

8. The medical device according to claim 6, wherein a back surface side of the first electrode, which does not contact the biological tissue, is also coated with the electrical insulation member.

9. A medical device for fusing a biological tissue, comprising:

a first electrode member and a second electrode member configured to sandwich the biological tissue between the first and second electrode members;

wherein said first electrode member comprises a flat plate-shaped electrode member;

wherein said second electrode member comprises two spaced apart needle-shaped electrode members;

an energy supply unit to supply electric energy between the two electrode members to effect the fusing of the biological tissue while the biological tissue is sandwiched between the first and second electrode members; and each of the first and second electrode members comprising an electrode surface which possesses a surface area, the surface area of the electrode surface of the first electrode member being different from the surface area of the electrode surface of the second electrode member;

wherein at least a portion of a ventral surface side of the first electrode is coated with an electrical insulation member;

wherein the biological tissue is a membrane member positioned between left and rights atriums of a heart, the membrane member being sandwiched between one of the first and second electrode members positioned on a left atrium side of the heart and the other electrode member positioned on a right atrium side of the heart, and wherein the electrical insulation member results in the entire conductive surface area of the electrode surface of the one electrode member on the left atrium side being larger than the entire conductive surface area of the electrode surface of the other electrode member on the right atrium side; and wherein the ratio (S1/S2) between the surface area (S1) of the entire conductive electrode surface of the other electrode member on the right atrium side and the surface area (S2) of the entire conductive electrode surface of the one electrode member on the left atrium side is more than 0.6 and less than 1.0.

10. The medical device according to claim 9, wherein at least the second electrode member is constructed to stick the biological tissue.

11. The medical device according to claim 9, wherein said two spaced apart needle-shaped electrode members are configured to diverge away from one another in a direction toward a distal end of the needle-shaped electrode members from a proximal end of the needle-shaped electrode members.

12. The medical device according to claim 9, wherein the first and second electrode members possess proximal end portions held at an attachment portion composed of an electrical insulation member.

13. The medical device according to claim 12, wherein the attachment portion is a catheter provided in a guiding catheter.

14. The medical device according to claim 9, wherein the first and second electrode members possess proximal end portions held at an attachment portion, and wherein at least one of the first and second electrode members is adjustable to vary the surface area of the electrode surface of the one electrode member by adjusting a protruding length of the one electrode member from the attachment portion.

15. The medical device according to claim 9, wherein the electrode surface of at least one of the first and second electrode members is coated with an electrically-conductive material, the electrically-conductive material being a material to which the biological tissue and blood or a thrombus are difficult to attach.

16. The medical device according to claim 9, wherein the medical device comprises a positioning mechanism for positioning the other electrode member at a predetermined position with respect to a foramen ovale.

17. The medical device according to claim 9, wherein the medical device comprises a positioning hold mechanism comprised of a positioning portion for positioning the other electrode member with respect to a foramen ovale and a holding portion for holding a foramen ovale valve so as to prevent a backward movement thereof with respect to a sticking direction of the other electrode member.

18. The medical device according to claim 9, wherein a back surface side of the first electrode, which does not contact the biological tissue, is also coated with the electrical insulation member.

* * * * *